United States Patent [19]
von Pragenau

[11] Patent Number: 5,239,864
[45] Date of Patent: Aug. 31, 1993

[54] DYNAMIC TESTER FOR ROTOR SEALS AND BEARINGS

[75] Inventor: George L. von Pragenau, Huntsville, Ala.

[73] Assignee: The United States of America as represented by the Administrator of the National Aeronautics and Space Administration, Washington, D.C.

[21] Appl. No.: 678,780

[22] Filed: Apr. 1, 1991

[51] Int. Cl.⁵ .................... G01M 15/00; G01N 19/00
[52] U.S. Cl. ............................. 73/118.1; 73/119 R; 73/865.9
[58] Field of Search ................ 73/118.1, 119 R, 49.7, 73/49.8, 662, 663, 665–668, 865.9

[56] References Cited

U.S. PATENT DOCUMENTS

| | | | |
|---|---|---|---|
| 2,906,991 | 9/1959 | Camp | 73/662 |
| 3,258,199 | 6/1966 | Anderson | 230/207 |
| 3,767,213 | 10/1973 | Cyphelly | 277/30 |
| 4,126,034 | 11/1978 | Conrad | 73/49.8 |
| 4,323,255 | 4/1982 | Wiese | 277/81 R |
| 4,644,202 | 2/1987 | Kroy et al. | 310/58 |
| 4,752,077 | 6/1988 | Hoffelner | 277/22 |
| 4,844,124 | 7/1989 | Stich et al. | 137/580 |
| 4,898,134 | 2/1990 | Breckenfeld et al. | 123/195 R |

FOREIGN PATENT DOCUMENTS

| | | | |
|---|---|---|---|
| 0257617 | 3/1988 | European Pat. Off. | 73/49.8 |
| 2233946 | 1/1974 | Fed. Rep. of Germany | 73/49.8 |
| 0282340 | 6/1971 | U.S.S.R. | 73/49.7 |
| 0386301 | 9/1973 | U.S.S.R. | 73/49.8 |
| 0911191 | 3/1982 | U.S.S.R. | 73/663 |
| 1339097 | 11/1973 | United Kingdom | 73/49.8 |

Primary Examiner—Hezron E. Williams
Assistant Examiner—George Dombroske
Attorney, Agent, or Firm—Robert L. Broad, Jr.; Guy M. Miller; John R. Manning

[57] ABSTRACT

A dynamic tester (10) for testing vibration damping seals and bearings is constructed having a hollow shaft (12) extending through the seal or bearing, with the shaft internally supported at each end by fluid bearings (19, 21) on hollow bosses (18, 20) connected to an interior of an enclosure (11), with no rolling members connected to the shaft. A high pressure working fluid is forced through the hollow bosses (18, 20) to operate the bearings. Additionally, the shaft (12) is provided with a reaction turbine (32) that angularly vents a portion of the high pressure working fluid in order to rotate the shaft at high speed, up top 40,000 rpm. The seal or bearing (44) is mounted in a bushing (70), in turn supported by rods (80, 82, 86 of FIG. 3, or rods 72, 74 of FIG. 2) coupled by flex hinges (90, 90a of FIG. 3, 76, 76a of FIG. 2) to a shaking device (92 of FIG. 3, or 78 of FIG. 2) that vibrates the seal or bearing as the shaft is rotated. A plurality of proximity sensors (100, 102, 104, 106, 108, 110, 112, 114) are mounted from outside the enclosure to sense shaft and seal bushing vibrations, and a plurality of pressure ports (120, 122, 124, 126, 128, 130, 132, 134) are disposed in the enclosure to allow sensing of dynamic and static pressures of the testing apparatus.

20 Claims, 2 Drawing Sheets

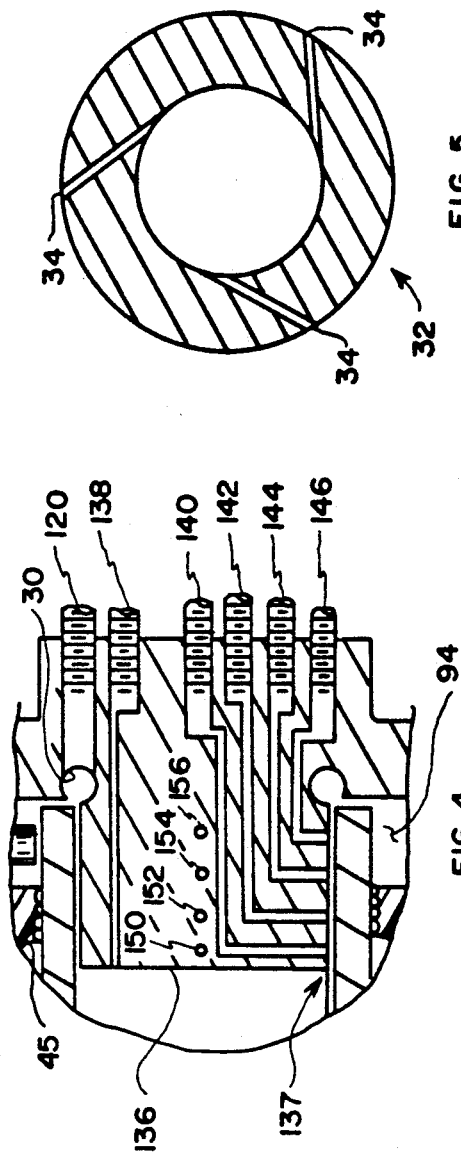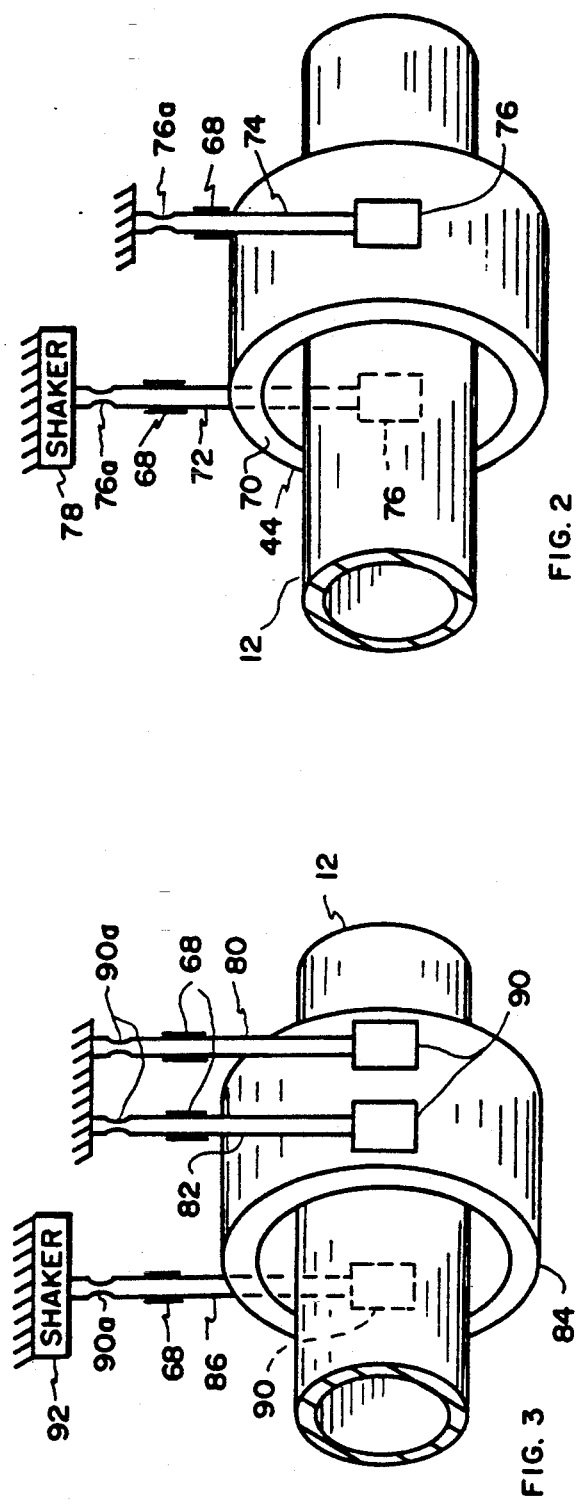

DYNAMIC TESTER FOR ROTOR SEALS AND BEARINGS

ORIGIN OF THE INVENTION

The invention described herein was made by an employee of the U.S. Government and may be manufactured and used by or for the Government for Government purposes without the payment of any royalties thereon or therefor.

FIELD OF THE INVENTION

This invention relates generally to high speed dynamic testers for annular bearings and seals and particularly to such a tester wherein a rotating hollow shaft extending through the test seals or bearings is supported between fluid bearings at each end, with the working fluid pressure for the bearings also driving a turbine that spins the shaft at high speed.

BACKGROUND OF THE INVENTION

High speed rotors and shafts, particularly those found in the hydrogen and oxygen turbopumps of the Space Shuttle Main Engines (SSME), are generally subject to vibrations and instabilities such as whirl instability, an orbital motion of high-speed shafts within bearings and seals, and which are generally due to tangential forces on the shaft. This whirling motion of a shaft is particularly damaging to bearings supporting the shaft, and necessitates use of damping seals and bearings that reduce or eliminate whirl instabilities and other undesirable vibrations. Another problem of high speed shafts is increased ball wear of ball bearings due to relatively high side loads applied to the shaft when in use, requiring expensive maintenance of the turbopumps. The damping bearings and gals also reduce this ball wear by reducing or eliminating these vibrations and size loads. These damping bearings and seals are developed and dynamically evaluated with a dynamic testing apparatus.

This testing apparatus uses a high speed steam turbine which spins a solid shaft supported by ball bearings, which shaft extending through the opening of the seal of bearing. A hydrostatic thrust bearing guides the test seal to prevent the seal from tilting, holding it in place such that a reciprocating shaker mechanism may vibrate the test seal. Shaker rods incorporating the strain gauges are tangentially attached to the seal bushing and to the shaker, and the shaker is operated in order to radially translate the seal or bearing. The resultant vibrations of the test seal or bearing are recorded and used to compute dynamic coefficients thereof.

this testing apparatus of the prior art is complex of construction, with the ball bearings of the high speed shaft being sensitive to any misalignment, necessitating expensive precision mounting in order to prolong life of the bearings. Additionally, the ball bearings are sensitive to transient interruptions of lubricant and coolant flow through the device. Also, connections to the shaker device are by mechanical linkages, including fork and clevis arrangements, which are subject to developing lash. Further, a number of seals are required to maintain separation between the high pressure test fluid, such as water, and lubrication oil and coolants. Additionally, the shaft of the tester, itself subject to axial loads and misalignment, configured such that pumps having a hollow shaft feed could not be simulated. Still further, the high pressures required for testing generated high axial thrusts on the test seal guide, causing rubbing. Also, the various fluids flowing through the tester and their attendant gals necessitated on longer shaft length, which in turn lowers the critical speed to approximately 10,000 rpm, at which whirl instabilities becomes a speed limiting factor of the test apparatus. Yet further, cryogenic fluids could not be tested because of the use of oil as a lubricant.

Accordingly, it is an object of this invention to provide a simpler and more reliable dynamic tester for damping seals and bearings wherein all rolling elements are eliminated and replaced by noncontacting, fluid bearings at each end of a hollow shaft and wherein axial thrusts are eliminated by use of a symmetrical reaction turbine to rotate the shaft. Additionally, the working fluid for the bearings is also used to drive the shaft via the turbine, allowing the shaft to be constructed shorter than the shaft of the device of the prior art and capable of much higher speeds well in excess of the aforementioned critical apes. Further, instrumentation is inserted and electrically connected to the tester from outside the tester, simplifying electrical connections and access to the instrumentation. Still further, a quadraplexed arrangement of the test seals allows tests with eccentric sleeves without overloading the fluid bearings. Also, the shaker rods are connected to the test seal and shaking device by flex hinges, which are not subject to developing lash.

SUMMARY OF THE INVENTION

An enclosure is provided with opposed, tubular hollow bosses through which a high pressure working fluid is forced, with a hollow shaft having fluid bearings at each end disposed to ride on exteriors of the opposed bosses. The shaft passes through a seal or bearing member mounted in the enclosure, which member is vibrated in order to dynamically evaluate it. A symmetrical turbine is fixed of the shaft and has drive elements exposed to thee high pressure working fluid such that the shaft is driven by the turbine at high rotational speeds.

BRIEF DESCRIPTION OF THE DRAWINGS

FIG. 2 is a diagrammatic view of particular details of construction of a portion of the present invention.

FIG. 3 is a diagrammatic view of an alternate embodiment of the present invention.

FIG. 4 is a cut-away view showing an alternate embodiment of a porting arrangement for measuring fluid pressures of a fluid bearing of the present invention.

FIG. 5 is a cut-away view taken along line 5—5 of FIG. 1 of a reaction turbine of the present invention.

DESCRIPTION OF THE PREFERRED EMBODIMENT

Figure 1:
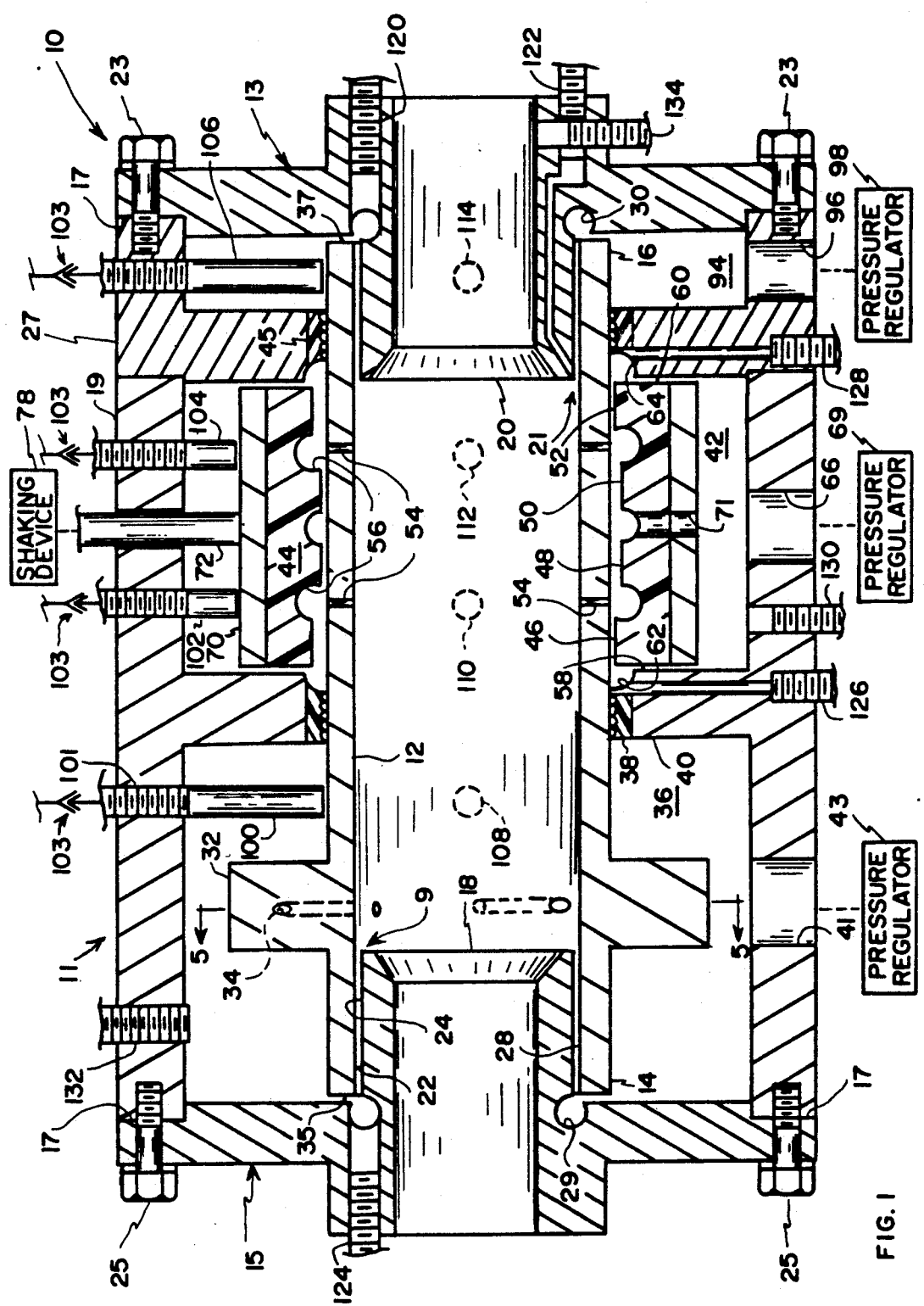
FIG. 1 is a cut-away view of the device of the present invention.

Referring to FIG. 1, a cut-away view of a dynamic seal and bearing tester 10 is shown. In this tester, a hollow, rotating shaft 12 is internally supported at ends 14 and 16 by inwardly extending, tubular hollow bosses 18 and 20, which in turn are constructed integral with end caps 13 and 15 of an enclosure 11. Enclosure 11 is constructed to be conveniently disassembled, with end caps 13 and 15 provided with flanges 17. Flanges 17 are constructed to closely fit cylindrical members 19 and 27 and end caps 13 and 15. A plurality of bolts 23 and 25 conventionally connect the components of enclosure 11, with at least some of bolts 23 extending through member 27 and threading into openings (not shown) in member 19. Constructed as such, enclosure 11 may be readily opened, proving convenient access for changing of seals and bearings.

Bosses 18 and 20 open into shaft 12 and provide a fluid path into shaft 12 at each end through which a high pressure working fluid, which may be water, a gas, or cryogenics such as liquid oxygen, hydrogen, or nitrogen, is forced. A small clearance retention 22 between an outer surface 24 of bosses 18 and 20 and inner surfaces 28 of each of ends 14 and 16 of shaft 12 form fluid bearings 9 and 21 at each end of shaft 12. Circumferential grooves 29 and 30 provide pressure equalization around bearings 9 and 21. In theses bearings, the flow of high pressure working fluid internally supports shaft 12 on bosses 18 and 20 is non-contacting relation therewith.

For producing rotation of shaft 12, a symmetrical reaction turbine 32 is rigidly fixed to shaft 12 and communicates via passageways 34 to the interior thereof. Backward slanting passageways 34 (more clearly shown in FIG. 5) direct a portion of the high pressure working fluid in angular relation from turbine 32, producing a reaction torque for driving shaft 12 at speeds of up to approximately 40,000 rpm, but typically this speed is regulated within design parameters f the seals or bearing. Alternately, a Pelton wheel or Bianchi (squirrel cage) turbine may be used to drive shaft 12, with the high pressure fluid directed to drive elements of the turbine from outside shaft 12 (not shown). Further, the turbine is symmetrical in design such that axial loads are avoided, with any axial loads produced being absorbed by fluid from stiffness of the working fluid in shaft end regions 35 and 37. Turbine 32 is enclosed within enclosure 11 in a turbine chamber 236, which is sealed from the rest of tester 10 by a labyrinth seal 38 set in a reduced diameter potion 40 of enclosure 11. Drive fluid from the turbine and from bearing 9 is vented from turbine chamber 36 through an opening 41, which is connected to a pressure-regulating device 43 that is adjustable to provide selected back pressures to chamber 36. This back pressure in chamber 36 reduces pressure differential between the working fluid in shaft 12 and the pressure in chamber 36, allowing rotational speed of the shaft to be closely controlled. Flow of working fluid through opening 41, which is the total flow of fluid through openings 34 of the turbine, and together with the working fluid pressure and angles of passageways connected to openings 34, may be used in calculations known in the part to determine total torque applied to shaft 12.

A test chamber 42 adjacent to chamber 36 is sealed on one side by the seal 38 and sealed on an opposite side by a second labyrinth seal 45. Chamber 42 houses a bushing 70 having a vent 71, bushing 70 disposed for supporting a damping seal 44 or, alternately, a bearing to be tested, with seal 44 illustrated herein by way of example. Shaft 12 extends through the opening in seal 44, which may be constructed such that a plurality of seal configurations to be tested by be built into one seal body, such as the quadraplexed seal surfaces 46, 48, 50, and 52 of seal 44. Additionally, opposed eccentricities, as seen by the positioning of seal surfaces 46 and 52 and contrasted to the positioning of surfaces 48 and 50, may be built into seal 44 for testing purposes. This opposed configuration of the quadraplexed eccentric seals helps reduce or eliminate radial forces applied to shaft 12 due to the eccentric seals. Openings 54 in shaft 12 communicate with interior grooves 56 in test seal 44, admitting working fluid to each of the seal configurations 46, 48, 50, and 52 of seal 44. Small clearance regions 58, 60 on each end of test seal 44 allows passage of working fluid leakage past test seal 44, which is evaluated, as will be explained. Additionally circumferential groves 62 and 64 in the chamber 42 function in the same manner as grooves 29 and 30 of bosses 18 and 20 by providing pressure equalization around sides of the seal. Fluids leaking past test seal 44 are vented from test chamber 42 through an opening 66, with the pressure drop of the test seal controlled by a back pressure regulating device 68 to vary the pressure differential across the test seals.

A third cavity 94, which receives leakage from bearing 20, is vented by opening 96, which may be provided with a back pressure regulating device 98 for adjusting the relative pressures between fluid bearings 9 and 21. Additionally, while the working fluid is shown as being introduced to tester 10 from hollow bosses 18 and 20, it is to be noted that flow of the working fluid may be reversed. In this situation, pressure regulators 43, 69, and 98 would be removed and the high pressure working fluid coupled to ports 41, 66, and 96, with the fluid exhausted through bosses 18 and 20. Turbine 32 would then operate to rotate shaft 12 in the opposite direction.

Test seal 44 is fitted into seal bushing 70, in turn supported in chamber 42, in one embodiment, by shaker rods 72 and 74 (FIG. 2) tangentially mounted to opposite sides of bushing 70 by flex hinges 76, which prevent chattering vibrations of the seal. Flex hinges 76 are each contiguous members and are not subject to wear as the mechanical linkages of the prior art, one or both of rods 72 and 74 may be connected, also using flex hinges, to a shaking device 678 that imparts selected loads to test seal 44 via rods 72 and 74. Wherein one of the rods is held rigid to prevent the bushing from spinning, and the other rod is translated, radial excursions of seal 44 are produced.

In another embodiment as shown in FIG. 3, a pair of rods 80 and 82 are tangentially mounted to one side of seal bushing 84, while a single rod 86 is mounted to the opposite side of the bushing, lending resistance to tilting forces applied to the seal and preventing the bushing from spinning. Again, either the pair of rods 80 and 82 or the single rod 86, or both, may be coupled by flex hinges 90a to shaking device 92. Strain sensors 68 attached to the rods sense the applied load and test seal torque from fluid rotation drag and produce electronic signals by which dynamic reactions to vibrations may be analyzed and effectiveness of damping functions of the seal determined.

For measuring deflections and vibrations of shaft 12 and test seal 44, a plurality of eddy-current type proximity probes are positioned closely adjacent o, generally on the order of 0.010", each end of shaft 12 and seal bushing 44, as shown in FIG. 1. Probes 100, 102, 104, and 106 are aligned to detect vibrations along points in a first plane of shaft 12 and seal bushing 670, while probes 108, 110, 112, and 114 (dotted lines) are arranged to monitor points along a plane normal to the first plane. These probes are installed, as by threads 101, from the exterior of tester 10 and electrically connected on the outside of apparatus 10 by conventional connectors, diagrammatically illustrated in FIG. 1 by connectors 103, simplifying maintenance of these probes and connections.

A number of pressure ports communicate with selected regions of test 10 and are disposed for providing pressure of the working fluid at these points to discrete pressure sensors (not shown). These pressure indications are used to evaluate sealing capabilities of seals under test and further provide information of operational parameters of tester 10. With respect to shaft 12, pots 120, 122, 124, and 134 are disposed to provide data relating to inlet pressure and discharge pressure of the fluid escaping through bearing regions 9 and 21 of shaft 12, and ports 126, 128 and 130 provide data relating to back pressure of working fluid leaking past ease seal 44. A pressure port 132 in enclosure 11 provides pressure of turbine chamber 36, which provides back pressure data in order to regulate rotational speed of shaft 12.

In the embodiment shown in FIG. 4, which illustrates a cut-away portion of end cap 13, the hollow boss 20 of FIG. 1 is replaced by a solid boss 136, with the opposite end cap 15 of apparatus 10 provided with the hollow boss 18 of FIG. 1. As such, apparatus 10 of this embodiment has a single high pressure inlet at boss 18, with the working fluid flowing around boss 136 and into chamber 94. Boss 136 is provided with an inlet pressure poet 138, which allows inlet pressure measurement of the high pressure fluid and a first plurality of ports 140, 142, 144, and 16 disposed to allow pressure measurement of the high pressure fluid passing around boxs 136. These ports are aligned in a plane with proximity probes 100, 102, 104, and 106. A second plurality of ports 150, 152, 154, and 156 are aligned in a plane with proximity probes 108, 110, 112, and 114 (FIG. 1). Pressure measurement as at these aligned ports and from port 120 of FIG. 1, allow determinations of radial loadign and dynamic static redaction forces on fluid pressure d bearing 136.

In accordance with the foregoing, it is apparent that the applicant has provided a seal and bearing tester that is simpler in construction than the tester of the prior art and one in which all rolling elements have between eliminated. Further, the shaft of the present invention is shorter than the shaft of the prior art, allowing higher rotation speeds.

Having thus described by invention and the manner of its use, it is apparent that various incidental changes and modifications may be made that fairly fall within the scope of the following appended claims, wherein I claim:

1. A testing apparatus for testing damping seals and bearings comprising:
   a housing having opposed, hollow bosses through which a high pressure working fluid is forced;
   a hollow, rotatable shaft mounted at each end over said bosses, said shaft having fluid bearing regions on sides of each said end such that said working fluid internally supports said shaft in noncontacting relation with said bosses;
   a symmetrically configured turbine rigidly mounted to said shaft and in communicating relation with an interior of said shaft, allowing said working fluid to react against drive elements of said turbine, rotating said shaft; and
   a bearing and seal support in said housing, for supporting an annular test member to be tested and having an opening through which said shaft rotatably extends such that vibrations due to shaft rotation may be measured.

2. A testing apparatus as set forth in claim 1 wherein said housing defines a turbine chamber enclosing said turbine therein, said turbine chamber having an opening for venting said working fluid therefrom.

3. A testing apparatus as set forth in claim 2 wherein said housing defines a test chamber enclosing said bearing and seal support, said test chamber sealed from said turbine chamber and having an opening for venting said working fluid from said test chamber 4. A testing apparatus as set forth in claim 3 comprising a vibration generating device coupled to said test member for selectively applying vibrational forces to said annular member.

5. A testing apparatus as set forth in claim 4 wherein flex hinges couple said vibration generating device to said the member.

6. A testing apparatus as set forth in claim 1 wherein ends of said shaft are provides with fluid bearing surfaces disposed for absorbing axial loads on said shaft.

7. A test apparatus as set forth in claim 3 comprising a first a pressure regulating device coupled to said opening of said turbine chamber, a second pressure regulating device coupled to said opening of said test chamber, for regulating back pressure in said turbine chamber and said test chamber.

8. A test apparatus as set forth in claim 7 comprising vibration measuring devices disposed for measuring vibrations of said shaft and said annular member.

9. A test apparatus as set forth in claim 1 wherein said annular member comprises a plurality of seal configurations to be tested and said shaft having openings therein communicating between said interior of said shaft to said plurality of seal configurations.

10. A test apparatus as set forth in claim 9 wherein said plurality of seal configurations include opposed eccentric seal configurations disposed about said shaft such that radial loading on said shaft is reduced.

11. A test apparatus as set forth in claim 1 comprising a plurality of pressure ports in said enclosure and disposed to provide selected pressures of the working fluid so that said pressures may be measured.

12. A testing apparatus for dynamic testing of damping bearing and seals, comprising;
   a generally hollow enclosure having a seal and bearing testing chamber therein, said seal and being testing chamber having a first opening for venting a pressurized working fluid from said chamber;
   a hollow, rotatable shaft extending through said test chamber and internally supported at each end by fluid bearings on opposed, hollow bases, with the pressurized working fluid introduced through said hollow bases;
   drive means coupled to said shaft and driven by said working fluid, for rotating shad shaft; and
   test seal and bearing support apparatus disposed for supporting a seal or bearing in said test chamber and on said shaft such that said seal or bearing is represented from rotating, and said test seal and bearing support apparatus further provided with means for providing selected translations of the support apparatus and said seal and bearing, and said test chamber having a second opening from which working fluid is vented.

13. A test apparatus as set forth in claim 12 wherein aid working fluid is provided through said first and second openings and is vented through said hollow bosses.

14. A test apparatus as set forth in claim 12 wherein said drive means comprises a symmetrical turbine, for reducing axial thrusts on said shaft, said turbine housed in a turbine chamber in said housing, said turbine chamber sealably isolated from said test chamber.

15. An apparatus as set forth in claim 12 comprising back pressure regulation means coupled to said openings of said test chamber and said turbine chamber, for regulating a pressure drop across said seal and for regulating rotational speed of said shaft.

16. An apparatus as set forth in claim 15 wherein said means for providing selected translations of the support apparatus is coupled to said test seal and bearing support apparatus by flex bins.

17. An apparatus as set forth in claim 16 wherein said support apparatus comprises a test seal bushing provided with first and second rods tangentially mounted on opposed sides of th bushing, with at least one of said rods coupled to said means for providing selected translations.

18. An apparatus as set forth in claim 16 wherein said support apparatus comprises a test seal bushing provided with a rod tangentially mounted on one side of said bushing and a pair of rods tangentially mounted on an opposed side of said bushing, for resisting tilting and spinning forces applied to said bushing, with at least one of said rod or said pair of rods coupled to said means for providing selected translations.

19. An apparatus as set forth in claim 18 comprising a plurality of proximity sensors positioned closely adjacent said shaft and said bushing and disposed for sensing excursions of said shaft and said bushing, said sensors installed, adjusted, and electrically coupled to equipment from outside said testing apparatus.

20. An apparatus as set forth in claim 12 wherein at least one of said fluid bearings is provided with a plurality of plots disposed to allow measurement of said working fluid at said fluid bearing.

* * * * *